US012608113B2

(12) United States Patent
Diaz et al.

(10) Patent No.: US 12,608,113 B2
(45) Date of Patent: Apr. 21, 2026

(54) MEDICAL RECORD SYSTEM USING A PATIENT AVATAR

(71) Applicant: Becton, Dickinson and Company, Franklin Lakes, NJ (US)

(72) Inventors: Oliver Crespo Diaz, Santa Clara, CA (US); Yuri Haverman, Franklin Lakes, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 16/084,187

(22) PCT Filed: Mar. 15, 2017

(86) PCT No.: PCT/US2017/022428
§ 371 (c)(1),
(2) Date: Sep. 11, 2018

(87) PCT Pub. No.: WO2017/160920
PCT Pub. Date: Sep. 21, 2017

(65) Prior Publication Data
US 2020/0293174 A1     Sep. 17, 2020

Related U.S. Application Data

(60) Provisional application No. 62/309,862, filed on Mar. 17, 2016.

(51) Int. Cl.
*G06F 3/04815*     (2022.01)
*A61B 5/00*     (2006.01)
(Continued)

(52) U.S. Cl.
CPC .......... *G06F 3/04815* (2013.01); *A61B 5/744* (2013.01); *G06F 3/011* (2013.01);
(Continued)

(58) Field of Classification Search
CPC .............. G06F 3/04815; G06F 3/0485; G06F 3/04842; G06F 3/04845; G06F 3/017;
(Continued)

(56) References Cited

U.S. PATENT DOCUMENTS 7,260,547 B2     8/2007  Kameda
7,890,498 B1 *   2/2011  Hafey .................... G16H 15/00
                                                      707/722
(Continued)

FOREIGN PATENT DOCUMENTS

CN          1443329 A          9/2003
CN        101530325 A          9/2009
(Continued)

OTHER PUBLICATIONS

International Search Report and Written Opinion mailed Jul. 11, 2017 in International Application No. PCT/US2017/022428.
(Continued)

*Primary Examiner* — Justin R. Blaufeld
(74) *Attorney, Agent, or Firm* — Knobbe, Martens, Olson & Bear, LLP

(57)     ABSTRACT

Disclosed is a medical system that allows a healthcare professional to view medical records as they are associated with a patient avatar. The system may create a three-dimensional view of an avatar representing a patient and attach patient records to specific locations of the avatar as representative of the data within each record. A timeline of treatments may be accessible by selecting a particular position on the avatar corresponding to medical treatments.

17 Claims, 5 Drawing Sheets

(51) Int. Cl.

| | | |
|---|---|---|
| *G06F 3/01* | (2006.01) | |
| *G06F 3/04842* | (2022.01) | |
| *G06F 3/04845* | (2022.01) | |
| *G06F 3/0485* | (2022.01) | |
| *G06Q 10/0631* | (2023.01) | |
| *G16H 10/60* | (2018.01) | |
| *G16H 15/00* | (2018.01) | |
| *G16H 50/50* | (2018.01) | |

(52) U.S. Cl.
CPC .......... *G06F 3/017* (2013.01); *G06F 3/04842* (2013.01); *G06F 3/04845* (2013.01); *G06F 3/0485* (2013.01); *G06Q 10/06316* (2013.01); *G16H 10/60* (2018.01); *G16H 15/00* (2018.01); *G16H 50/50* (2018.01)

(58) Field of Classification Search
CPC ........ G16H 10/60; G16H 50/50; G16H 15/00; G06Q 10/06316
See application file for complete search history.

(56) References Cited

U.S. PATENT DOCUMENTS

| | | | | |
|---|---|---|---|---|
| 11,061,537 | B2* | 7/2021 | Sahu | G06F 3/0485 |
| 2001/0041992 | A1* | 11/2001 | Lewis | G16H 70/00 |
| | | | | 705/3 |
| 2009/0192823 | A1* | 7/2009 | Hawkins | G06Q 10/06 |
| | | | | 715/767 |
| 2012/0127157 | A1* | 5/2012 | Adler | G06Q 10/00 |
| | | | | 345/419 |
| 2012/0182291 | A1 | 7/2012 | Rawat et al. | |
| 2012/0249741 | A1* | 10/2012 | Maciocci | G06T 19/006 |
| | | | | 348/51 |

| | | | | |
|---|---|---|---|---|
| 2012/0299818 | A1* | 11/2012 | Li | G06F 3/0484 |
| | | | | 345/156 |
| 2013/0117707 | A1* | 5/2013 | Wheeler | G06F 3/012 |
| | | | | 715/784 |
| 2013/0325493 | A1 | 12/2013 | Wong et al. | |
| 2013/0326364 | A1* | 12/2013 | Latta | G06F 3/012 |
| | | | | 715/751 |
| 2014/0081659 | A1 | 3/2014 | Nawana et al. | |
| 2014/0140591 | A1* | 5/2014 | Arazi | G06T 7/0012 |
| | | | | 382/128 |
| 2014/0304005 | A1* | 10/2014 | Hughes | G06F 3/041 |
| | | | | 705/2 |
| 2015/0278483 | A1* | 10/2015 | Pruitt | G16H 10/60 |
| | | | | 705/3 |
| 2015/0306340 | A1 | 10/2015 | Glap et al. | |

FOREIGN PATENT DOCUMENTS

| | | |
|---|---|---|
| CN | 102165306 A | 8/2011 |
| CN | 102955901 A | 3/2013 |
| CN | 102959579 A | 3/2013 |
| CN | 103562846 A | 2/2014 |
| CN | 103886174 A | 6/2014 |
| JP | 2004-005565 | 1/2004 |
| JP | 2004/529401 | 9/2004 |
| JP | 2012-110717 A | 6/2012 |
| JP | 2015-062119 A | 4/2015 |
| JP | 2015-099184 A | 5/2015 |
| WO | WO 2015/134953 A1 | 9/2015 |

OTHER PUBLICATIONS

International Preliminary Report on Patentability issued Sep. 18, 2018 in International Application No. PCT/US2017/022428.

* cited by examiner

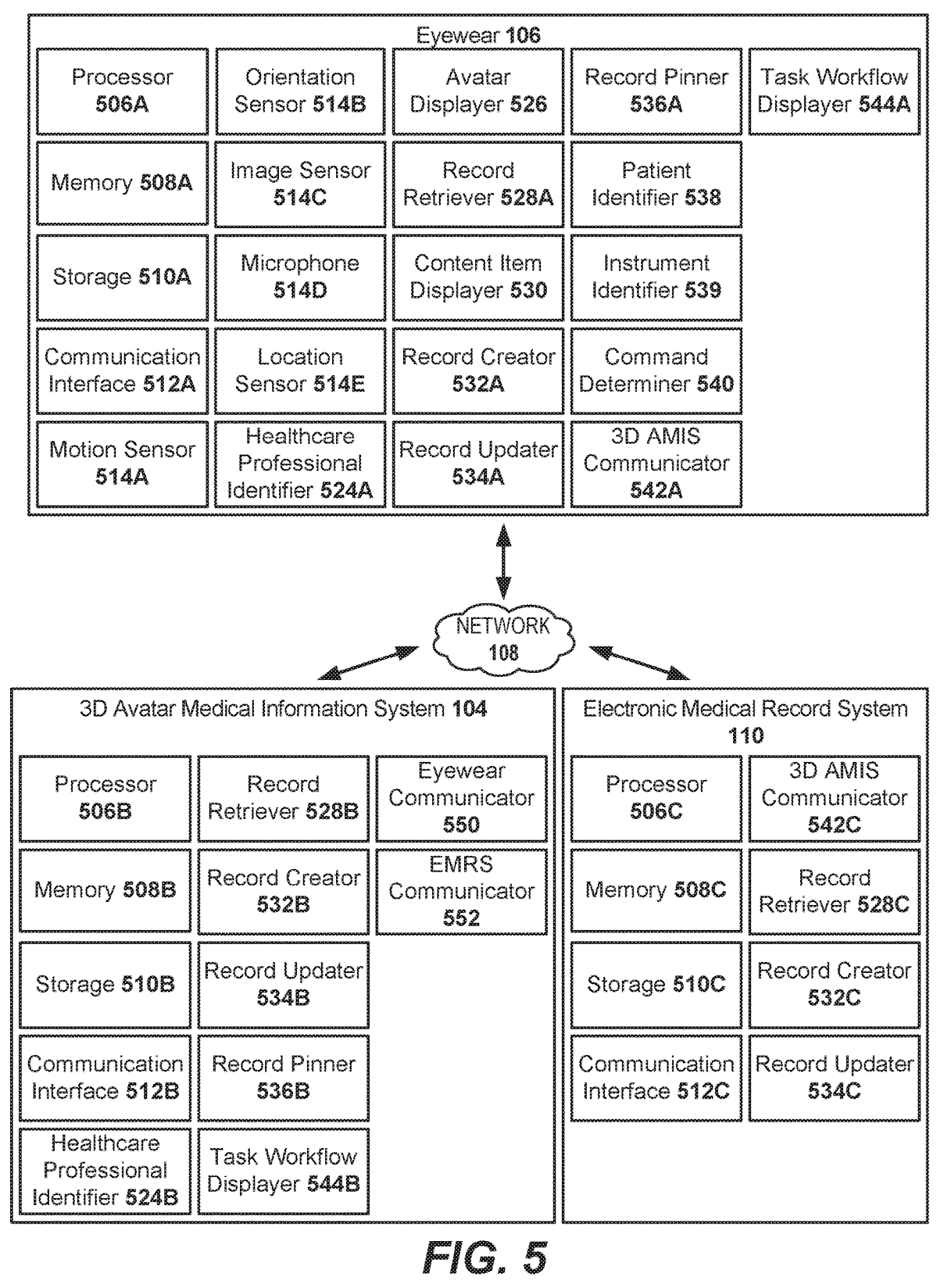

| Eyewear 106 | | | | |
|---|---|---|---|---|
| Processor 506A | Orientation Sensor 514B | Avatar Displayer 526 | Record Pinner 536A | Task Workflow Displayer 544A |
| Memory 508A | Image Sensor 514C | Record Retriever 528A | Patient Identifier 538 | |
| Storage 510A | Microphone 514D | Content Item Displayer 530 | Instrument Identifier 539 | |
| Communication Interface 512A | Location Sensor 514E | Record Creator 532A | Command Determiner 540 | |
| Motion Sensor 514A | Healthcare Professional Identifier 524A | Record Updater 534A | 3D AMIS Communicator 542A | |

NETWORK 108

| 3D Avatar Medical Information System 104 | | |
|---|---|---|
| Processor 506B | Record Retriever 528B | Eyewear Communicator 550 |
| Memory 508B | Record Creator 532B | EMRS Communicator 552 |
| Storage 510B | Record Updater 534B | |
| Communication Interface 512B | Record Pinner 536B | |
| Healthcare Professional Identifier 524B | Task Workflow Displayer 544B | |

| Electronic Medical Record System 110 | |
|---|---|
| Processor 506C | 3D AMIS Communicator 542C |
| Memory 508C | Record Retriever 528C |
| Storage 510C | Record Creator 532C |
| Communication Interface 512C | Record Updater 534C |

*FIG. 5*

MEDICAL RECORD SYSTEM USING A PATIENT AVATAR

CROSS-REFERENCE TO RELATED APPLICATIONS

The present application is a U.S. national phase application under 35 U.S.C. § 371 of International Application No. PCT/US2017/022428, filed Mar. 15, 2017 and published in English as WO 2017/160920 on Sep. 21, 2017, which claims priority to U.S. Provisional Application No. 62/309,862, filed on Mar. 17, 2016. The content of each of these related applications is incorporated herein by reference in its entirety.

BACKGROUND OF THE INVENTION

Field of the Invention

The invention relates to medical information systems, and more particularly, relates to methods and systems for displaying medical information using a 3D avatar.

Description of the Related Art

During the course of a doctor visit or a hospital visit, a doctor examines a patient and then documents that encounter in a medical information system. During such an encounter, a large amount of medical information can be generated by the doctor that needs to be quickly and accurately stored in the patient's medical record. The medical information stored may include, for example, medical data generated by medical instruments and sensors attached to the patient.

The doctor may either type or dictate his notes into the medical information system. However, such typing and dictation can take a long time, and may not accurately link all of the different types of information recorded by the doctor in a simple and convenient format for later retrieval.

SUMMARY OF THE INVENTION

Disclosed herein are devices and methods for displaying and recording medical information using a patient avatar. In one example, the device includes: one or more sensors; a processor operably coupled to the one or more sensors; and a memory component, operably coupled to the processor, the processor and memory component being collectively configured to: display a 3D patient avatar; and display a first content item of medical information on the 3D avatar. In one example, the method includes: displaying a 3D avatar; and displaying a first content item of medical information on the 3D avatar.

BRIEF DESCRIPTION OF THE DRAWINGS

FIG. 5 is a block diagram depicting an illustrative operating environment of the holographic eyewear, the 3D avatar medical information system, and the electronic medical record system.

DETAILED DESCRIPTION

Figure 1:
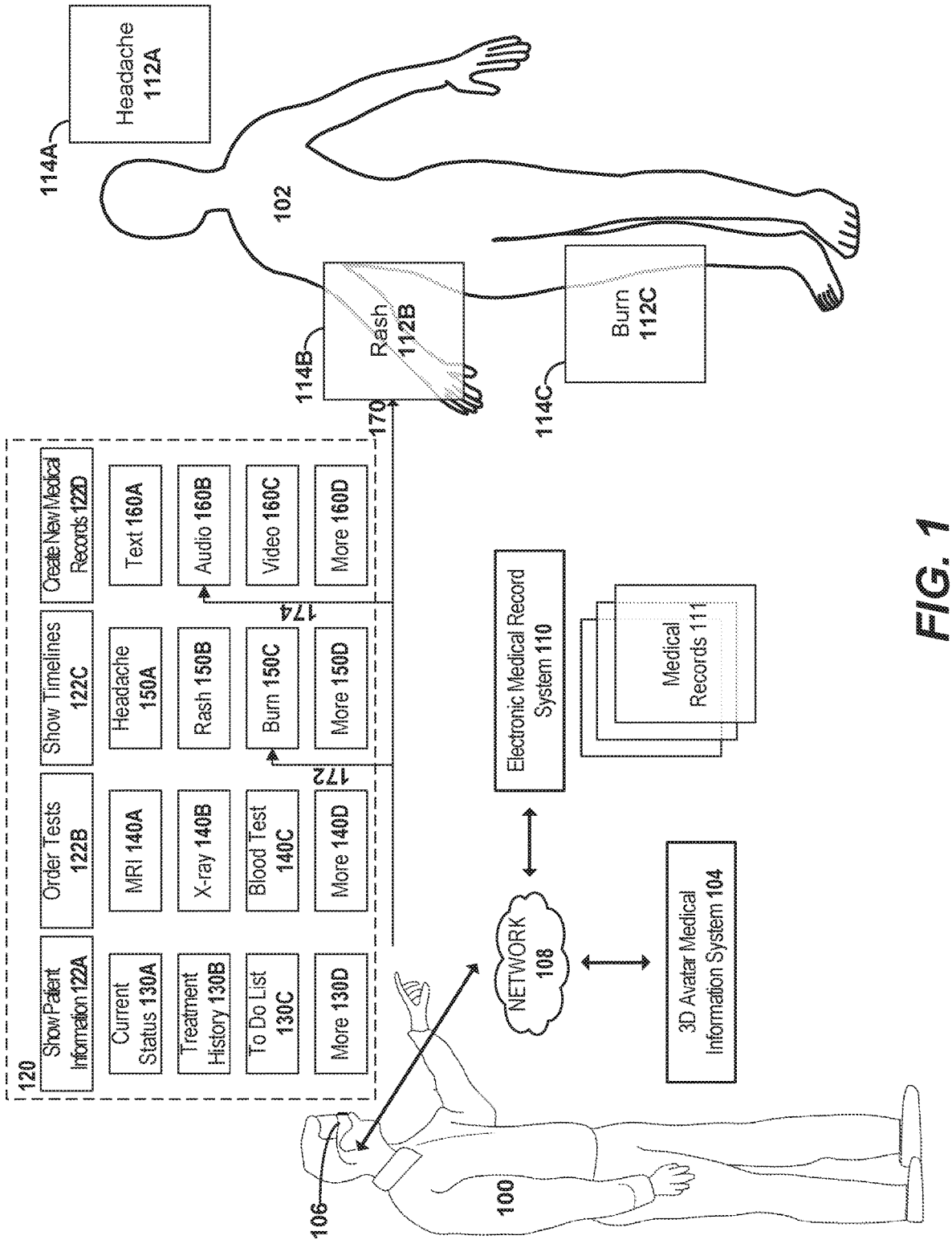
FIG. 1 is a schematic illustration showing exemplary interactions between a healthcare professional and medical information using a 3D avatar implemented by a 3D avatar medical information system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Various persons, including, but not limited to, physicians, nurses, healthcare professionals, healthcare providers, healthcare administrative staffs, and hospital administrators can operate or make use of illustrative embodiments of the 3D avatar medical information system disclosed herein. For brevity these users are referred to as "healthcare professionals" hereinafter. Healthcare professionals can be users of the 3D avatar medical information system. Patients can also be users of the 3D avatar medical information system.

Embodiments of the invention relate to systems and methods for presenting a healthcare professional with a three-dimensional representation of a patient, referred to as a "3D avatar". The 3D avatar can be viewed when the healthcare professional wears a special headset, visor, glasses, eyewear, or looks at a specially produced display, configured to display three dimensional images. The 3D avatar represents a human body in three dimensions. The 3D avatar can be used to link medical information of the patient to a specific site on the patient. For example, a patient recovering from left knee surgery may visit a physician. The physician may put on a holographic eyewear configured as described below to produce a 3D avatar image representing the patient's medical record. The physician will see a graphical indicium of a file associated with the left knee position on the avatar. The eyewear system will be able to record the position of the physician's fingers. The eyewear system can determine if the physician has touched the graphical indicium of the file image associated with the left knee. If the eyewear system determines that the physician has selected the file associated with the left knee, it may display surgery records, such as x-rays, notes, surgery details, and other information associated with the patient's left knee. This allows the system to conveniently and intuitively store medical information for a particular patient in a manner that is easy for the physician to access and understand.

It should be realized that two-dimensional "2D" and three-dimensional "3D" avatars are non-limiting examples of the one or more interactive images for managing patient healthcare. In some embodiments, the systems and methods disclosed herein make use of a 3D avatar for capturing patient medical information and for medical record keeping. The 3D avatar can be a holographic 3D avatar. Non-limiting examples of technologies for implementing the methods and systems disclosed herein include mixed reality technology, augmented reality technology, and virtual reality technology.

System Architecture

FIG. 1 is a schematic illustration showing exemplary interactions between a healthcare professional 100 and medical information using a 3D avatar 102 implemented by a 3D avatar medical information system (3D AMIS) 104. The healthcare professional 100 can interact with the 3D avatar medical information system 104 using a holographic eyewear 106 that is configured to display 3D representations of the avatar or other information. Microsoft® HoloLens® is a non-limiting example of one type of holographic eyewear that may be used within embodiments of the invention. Other non-limiting examples of the holographic eyewear include Google Glass®, Oculus Rift®, Sony® Glasstron™, and HTC Vive®.

The holographic eyewear 106 generally includes two lenses, one for each of the healthcare professional's eyes in order to present a 3D image within the healthcare professional's field of view. The holographic eyewear 106 can display information, for example medical information, to the healthcare professional 100 via the two lenses. In some embodiments, the holographic eyewear 106 can communicate with to the healthcare professional 100 using one or more audio devices (e.g., speakers and earphones), in wired or wireless communication with the holographic eyewear 106.

The holographic eyewear 106, using one or more sensors in wired or wireless communication with the holographic eyewear 106, is configured to monitor and determine the healthcare professional's commands or instructions. The healthcare professional 100 can give commands to the holographic eyewear 106 using his gesture. Additionally or alternatively, the healthcare professional 100 can give commands to the holographic eyewear 106 using the movements of his fingers, hands, arms, or legs (or any body part) or other objects connected with the healthcare professional 100.

The holographic eyewear 106 can be in wired or wireless communication with the 3D avatar medical information system 104 through a network 108. The 3D avatar medical information system 104 can be configured to retrieve medical information, for example medical records, from an electronic medical record system (EMRS) 110 for display by the holographic eyewear 106 to the healthcare professional 100. The medical information retrieved from the electronic medical record system 110 can be captured and recorded by two or more pairs of the holographic eyewear 106 and/or two or more of the 3D avatar medical information systems 104. In some embodiments, the medical information retrieved from the electronic medical record system 110 can be captured and recorded by systems other than the holographic eyewear 106 and the 3D avatar medical information system 104. Non-limiting examples of the medical information captured and recorded by such systems include medical instruments not part of the 3D avatar medical information system 104, for example MRI machines, X-ray machines, and blood analysis instruments.

In some embodiments, two or more healthcare professionals and patients can simultaneously interact with the 3D avatar medical information system 104 using two or more pairs of the holographic eyewear 106. The two or more healthcare professionals 100 may be in close proximity or far from one another, and the system may link them to one another though the network 108.

3D Avatar

In one embodiment, a 3D avatar 102 can be displayed with medical information of a patient. The medical information of the patient can be displayed as appearing on top of or behind the 3D avatar 102. The medical information of the patient can be displayed as overlapping or adjacent the 3D avatar 102. The medical information displayed can include some or all of the patient's medical information stored in the electronic medical record system 110. The medical information displayed can be captured and recorded during the patient's current or previous doctor or hospital visits. The medical information displayed can be related to a disease, an instance of a disease, a group of related diseases, or a medical specialty.

Medical Records

The medical information can include medical records 111. The holographic eyewear 106, using its one or more lenses, can display the medical records 111 as the medical record content items 114A-C to the healthcare professional 100. The medical records 111 can be displayed together with the 3D avatar 102. The medical records 111 displayed can be grouped together based on, for example, the disease type, disease severity, symptoms, disease progression and healing, medical specialty. The medical records 111 displayed can be grouped based on the doctors creating the medical records 111 or the hospital visits during which the medical records 111 are created. FIG. 1 shows that the medical records 111 can be grouped into medical information categories 112 by disease types: "headache" 112A, "rash" 112B, and "burn" 112C. The medical records 111 of categories 112A, 112B, and 112C can be displayed as medical record content items 114A, 114B, and 114C respectively. A medical record content item can include previews of the medical records 111.

The holographic eyewear 106 is configured to display the recorded content items 114A-C at different geographical locations relative the 3D avatar 102. The 3D avatar medical information system 104 can determine the locations of the medical record content items 114A-C by reference to data stored in the medical records. In some embodiments, the locations of the medical record content items 114A-C are determined by healthcare professionals when creating the medical record content items 114A-C. In some embodiments, the locations of the medical record content items 114A-C are determined by healthcare professionals for existing medical record content items without location information determined when they are captured and first recorded.

The medical record content items 114A-C can be displayed, for example, as appearing on top of the 3D avatar 102, overlapping the 3D avatar 102, behind the 3D avatar 102, or adjacent the 3D avatar 102. In some embodiments, the medical record content items 114A-C can be displayed as appearing spatially near locations on the 3D avatar 102 that correspond to organ locations of a person, for example the 3D avatar's head, arm, leg, kidney, or liver. The healthcare professional 100 can move the medical record content items 114A-C to different pinning locations relative to the 3D avatar 102 as desired or required to reflect, for example, patient status and disease progression and healing. For example, to move the medical record content item 114C from the right knee to the left knee of the 3D avatar 102, the healthcare professional 110 can "touch" a graphical indicium representing the medical record content item 114C with one or more of his fingers, and move his one or more fingers from the right knee to the left knee of the 3D avatar 102. The holographic eyewear 106 can include one or more image sensors for capturing such a "touch" and "movement."

As illustrated in FIG. 1, the medical record content item 114A of the "headache" category 112A can be displayed as appearing spatially near the head of the 3D avatar 102, where the patient has suffered or is suffering a headache. The medical record content item 114B of the "rash" category 112B can be related to a rash on the right forearm of the patient, and the medical record content item 114B can be displayed as appearing on top of the right forearm of the 3D avatar 102. The medical record content item 114C of the "burn" category 112C can be related to a burn on the right kneecap, and the medical record content item 114C can be displayed overlapping the right kneecap of the 3D avatar 102.

Non-limiting examples of the type of data that can be included within the stored medical records 111 include text data, 2D data, 3D data, audio data, video data, or any combination thereof. The medical records 111 can include real time data, for example, real time MRI data while the data is still being collected. The medical records 111 can be text data on the severity and duration of a disease or symptom; treatment history, including drug dosage, timing, and result; and a patient's family history on the disease or symptom. Text data can be notes and observations by healthcare professionals and patients. Text data can include test results and patient information. Patient information can include name, address, phone number; contact information for next of kin; primary care physician's name, address, and phone number; date of birth; eye color; glasses prescription; use of contact lenses; blood type; allergies; medications, both dosage and frequency; procedures and surgeries, both associated dates and outcomes; family medical history; diabetes conditions; pacemaker usage, history, and model; disease symptoms, for example symptoms of Alzheimer; presence of heart stents; use of pain pumps; cancer history; chemotherapy type, period, course, and history; use of hearing aids; presence of dentures; insurance information; vaccination history; childhood illnesses; colonoscopy results; or any combination thereof.

2D data and 3D data can include the patient's photo ID; fingerprints; eye images; biometric information; sonogram; dental X-rays; optical images of skin moles; computed tomography ("CT"); positron emission tomography ("PET"); single photon emission computed tomography ("SPECT"); ultrasound ("US"); X-ray; mammography; magnetic resonance imaging ("MRI"); diffusion tensor imaging ("DTI"); magnetic resonance angiogram ("MRA"); computerized tomographic angiography (CTA); medical optical imaging ("MOI") such as computed optical tomography ("COT"); neutron stimulated emission computed tomography ("NSECT"); dual-energy x-ray absorptiometry ("DEXA"); digital radiography; ductography; ultrasonography; thermography; electrical impedance tomography; magnetoencephalography ("MEG"); electrocardiogram ("EKG"); electroencephalogram ("EEG"); or any combination thereof. Audio data can be audio recordings of healthcare professionals and patients. Video data can be video recordings of procedures performed by healthcare professionals and patients' behaviors.

In some embodiments, the medical records 111 can be provided by patients, for example verbally. The medical records 111 can be inputted by healthcare professionals into the 3D avatar medical information system 104 for storage in the electronic medical record system 110. In some embodiments, the medical records 111 can be retrieved by the 3D avatar medical information system 104 from the electronic medical record system 110. The medical records 111 retrieved by the 3D avatar medical information system 104 from the electronic medical record system 110 can include medical records 111 created by other healthcare professionals, including healthcare professionals of various specialties and at different hospitals, cities, states, and countries. The medical records 111 retrieved from the electronic medical record system 110 can be recorded at the same time or different times.

User Menu

The holographic eyewear 106 can display a user menu 120. The user menu 120 can be displayed as appearing on top of the 3D avatar 102, overlapping the 3D avatar 102, behind the 3D avatar 102, or adjacent the 3D avatar 102. The user menu 120 can include main menu content items, such as "show patient information" 122A, "order tests" 122B, "show timelines" 122C, and "create new medical records" 122D. The "show patient information" main menu content item 122A can include submenu content items such as show "current status" 130A, "treatment history" 130B, "to do list" 130C, and "more" patient information 130D. The "order tests" main menu content item 122B can include submenu content items 140 uch as order "MRI" 140A, "X-ray" 140B, "blood test" 140C, and "more" tests 140D.

The "show timelines" main menu content item 122C can include submenu content items for showing timelines of the medical records 111, for example, displayed on the 3D avatar 102. The submenu content items can group medical records 111 for display based on the medical information categories 112A-C. For example, the "show timelines" main menu content item 122C can include submenu content items for showing timelines of the "headache" category 112A as a submenu content item 150A, the "rash" category 112B as a submenu content item 150B, the "burn" category 112C as a submenu content item 150C, and "more" medical information category as a submenu content item 150D. The "create new medical records" main menu content item 122D can include submenu content items for creating new medical records of various data types, for example creating a new "text" medical record 160A, a new "audio" medical record 160B, a new "video" medical record 160C, and "more" types of medical records 160D.

Content items include the main menu content items 122A-D, submenu content items 130A-D, 140A-D, 150A-D, and 160A-D, and the medical records content items 114A-C. The various content items can include or associated with an icon, image, medical record, text data, 2D data, 3D data, audio data, video data, preview, summary, or any combination thereof.

Interactions between Healthcare Professional and 3D Avatar Medical Information System A healthcare professional 100 can interact with the 3D avatar medical information system 104 by interacting with the 3D avatar 102 and the user menu 120, for example, by "touching" the various content items by raising and pressing a finger on a displayed image associated with a content item. For example, to see more information of the "rash" category 112B, the healthcare professional 100 can "touch" 170 the medical record content item 114B of the "rash" category 112B as it appears to be floating in space in front of the 3D avatar 102. To see the medical records 111 of the "burn" category 112C shown as a timeline, the healthcare professional 100 can "touch" 172 the submenu content item 150C corresponding to the medical records 111 of the "burn" category 112C. To create new medical records, the healthcare professional 100 can "touch" 174 the submenus content item 160B for creating a new "audio" medical record. The ability to interact with the various content items appearing in space may be controlled by image sensors (e.g., cameras) in the headset that determines the position of the healthcare professional's fingers at they move in three-dimensional space.

Other non-limiting examples of the interactions between the healthcare professional 100 and the 3D avatar medical information system 104 include zoom in and zoom out on the 3D avatar 102, rotate the 3D avatar 102, and orient the 3D avatar 102. When the healthcare professional 100 wants to zoom in or zoom out on the 3D avatar 102, the healthcare professional 100 he can "touch" the 3D avatar 102 with two of his fingers and "move" these two fingers away from or closer to each other. When the holographic eyewear 106 determines that such a "touch" and "movement" have occurred, the holographic eyewear 106 can display an enlarged or smaller 3D avatar 102 to the healthcare professional 100.

Touch

The healthcare professional 100 "touches" a content item when the healthcare professional 100 sees, through the holographic eyewear 106, that one or more of his fingers, hands, arms, legs, or one or more objects he is connected with, come into contact with a graphical display representing the content item. The holographic eyewear 106 determines that such a contact has occurred using, for example, image sensors of the holographic eyewear 106. When the holographic eyewear 106 determines that such a contact has occurred, the holographic eyewear 106 can update the display shown to the healthcare professional 100 based on the programmed response to the content item that the healthcare professional 100 has "touched."

Interactions between Healthcare Professional and 3D Avatar

Figure 2:
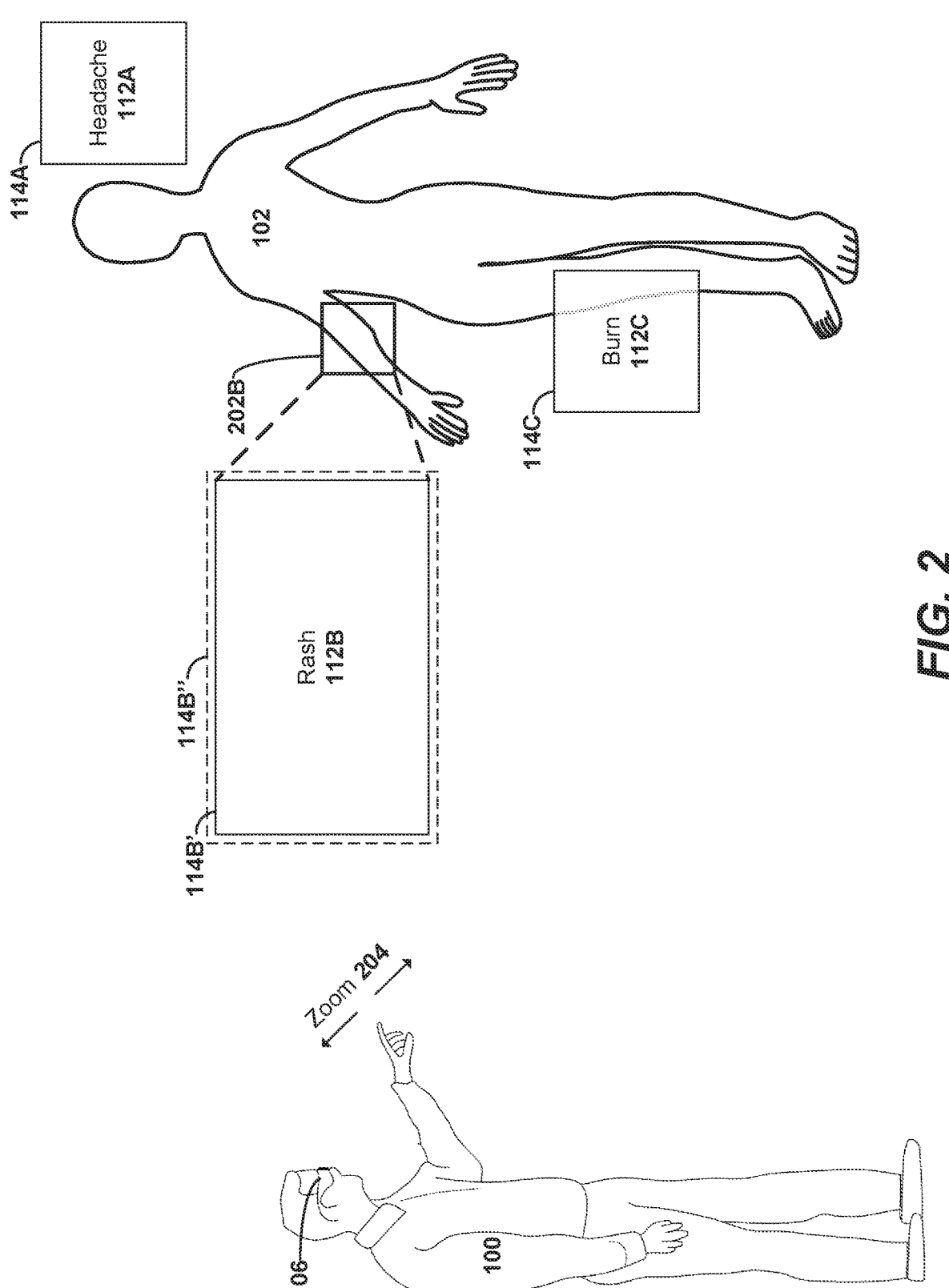
FIG. 2 is a schematic illustration showing exemplary interactions between a healthcare professional and a medical record.

FIG. 2 is a schematic illustration showing exemplary interactions between a healthcare professional 100 and a medical record displayed on a 3D avatar 102. To obtain more information of the "rash" category 112B, the healthcare professional 100 can "touch" a displayed graphical representation or indicium of the medical record content item 114B of the "rash" category 112B. When the holographic eyewear 106 determines that the healthcare professional 100 has "touched" 170 the displayed graphical representation of the medical record content item 114B of the "rash" 112B, the holographic eyewear 106 can update the display shown to the healthcare professional 100 based on the medical record content item 114B "touched." FIG. 2 illustrates the updated display shown to the healthcare professional 100 in some embodiments of the present disclosure.

The updated medical record content item 114B' can be an enlarged version of the medical record content item 114B. In some embodiments, the updated medical record content item 114B' can show more detailed medical records of the "rash" category 112B to the healthcare professional 100. The holographic eyewear 106 can indicate that the medical record content item 114B' is related to the rash on the right forearm of the patient by, for example, highlighting the right forearm by a highlight box 202B.

Once the holographic eyewear 106 displays the updated medical record content item 114B' to the healthcare professional 100, he can interact with it. For example, the healthcare professional 100 can zoom in on the updated medical record content item 114B' by, for example, the movements of his fingers. When the healthcare professional 100 wants to zoom in on the updated medical record content item 114B', he can "touch" a displayed graphical representation of the updated medical record content item 114B' with two of his fingers and "move" these two fingers away from each other 204. When the holographic eyewear 106 determines that such a "touch" and "movement" have occurred, the holographic eyewear 106 can display an updated medical record content item 114B". The updated medical record content items 114B' and 114B" can have the same size or different sizes. Other non-limiting examples of the interactions between the healthcare professional 100 and the 3D avatar medical information system 104 include zoom out, click and expand, and return to the user menu 120.

Disease Timeline

Figure 3:
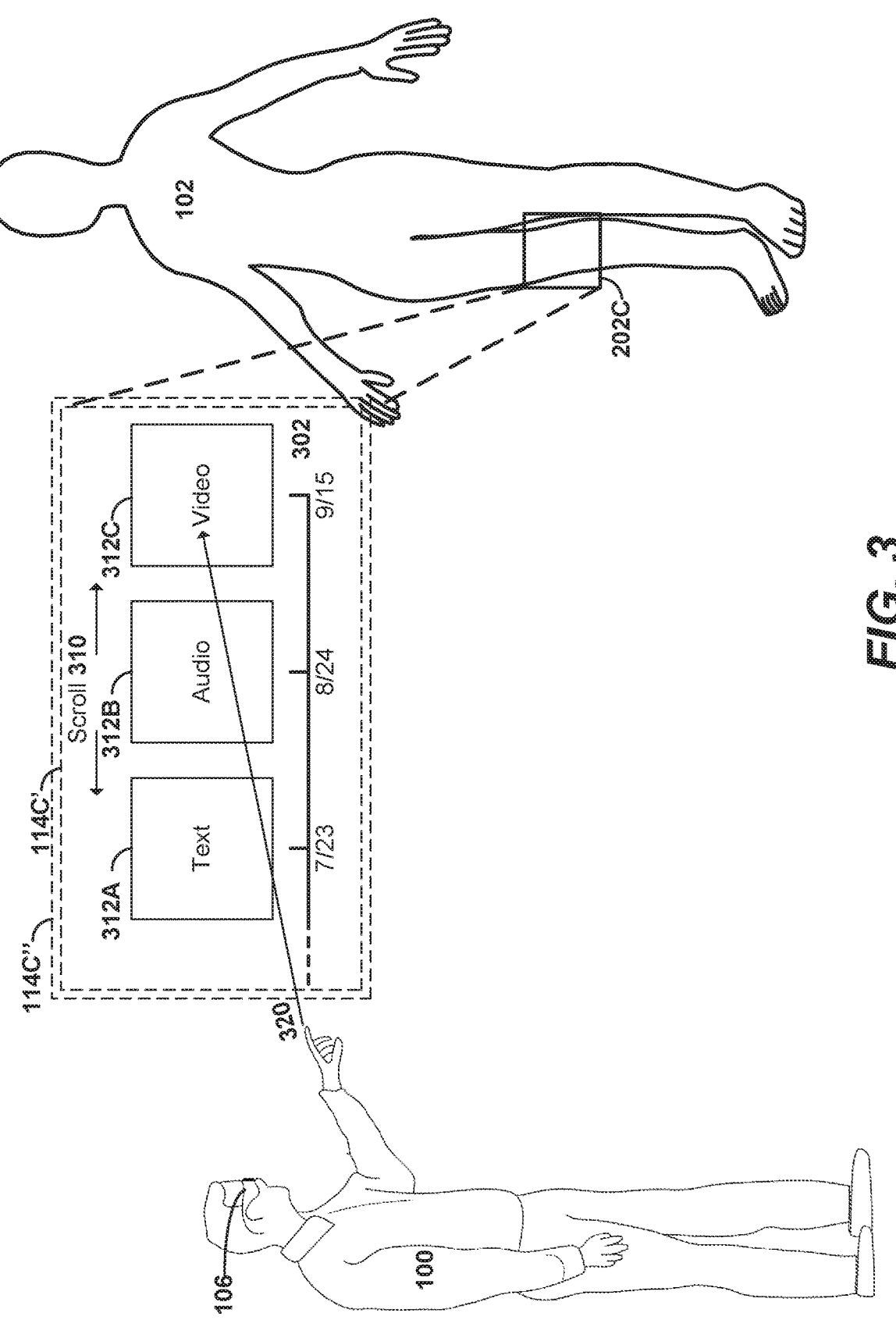
FIG. 3 is a schematic illustration showing exemplary interactions between a healthcare professional and a disease timeline.

FIG. 3 is a schematic illustration showing exemplary interactions between a healthcare professional 100 and a disease timeline. To see the records associated with a highlight box 202C or the records displayed or summarized in highlight box 202C, the healthcare professional 100 can "touch" a submenu content item of the "burn" category. The system may display a timeline 302 that includes information relating to the burn over time. The timeline 302 allows the healthcare professional 100 to monitor the patient's disease progression and recovery and to determine whether a different course of treatment is feasible or desirable. The timeline 302 can organize and display the medical records in a visual and intuitive way over time based on where on the body each medical issue was diagnosed. When the patient returns for a subsequent doctor visit or hospital visit, the healthcare professional 100 can examine the timeline 302 of medical records from previous visits. In some embodiments, the healthcare professional 100 can scroll through the timeline 302 to review the various medical records from the previous visits.

The updated medical record content item 114C' having a timeline 302 can include multiple medical record content items of various data types, for example text data, 2D data, 3D data, audio data, video data, previews, summaries, or any combination thereof. For example, FIG. 3 shows three medical record content items 312A-312C in the updated medical record content item 114C'. The medical record content items 312A-312C can be text data, audio data, and video data respectively. The medical record content items 312A-312C can represent a timeline of the patient's disease progression and recovery at different time points. For example, the text data of the medical record content item 312A can be written notes and observations by the healthcare professional 100 regarding the burn at a first time point, for example July 23. The audio data of the medical record content item 312B can be audio notes and observations by the healthcare professional 100 regarding the burn at a second time point subsequent to the first time point, for example August 24. The video medical record, displayed as the medical record content item 312C, can include video data of the burn at a third time point subsequent to the first and second time points, for example September 15.

The holographic eyewear 106 can show that the medical record content item 114C' is related to the burn on the right kneecap by, for example, highlighting the right kneecap with the highlight box 202C. Once the holographic eyewear 106 displays the updated medical record content item 114C' to the healthcare professional 100, he can interact with it. For example, the healthcare professional 100 can look at medical record content items prior to the first time point of the medical record content item 302 shown by, for example, scrolling 310 with the movements of his fingers. When the healthcare professional 100 wants to scroll 310, he can "touch" a graphical indicium of the updated medical record content item 114C' with one of his fingers and "move" the finger to the left, for example, corresponding to a time point prior to the first time point of the medical record content item 312A. Image sensors on the eyewear 106 can monitor and capture that movement of the finger to determine that the healthcare professional 100 wishes to review records other than the displayed records. Once the holographic eyewear 106 determines that such a "touch" and "movement" have occurred, the holographic eyewear 106 can display an updated medical record content item 114C".

In some embodiments, the healthcare professional 100 can watch the video medical record of the medical record content item 312C by, for example, the movements of his fingers. When the healthcare professional 100 wants to watch the video medical record of the medical record content item 312C, he can "touch" 320 the medical record content item 312 with one of his fingers. Once the holographic eyewear 106 determines that such a "touch" has occurred, the holographic eyewear 106 can display the video medical record of the medical record content item 312C. Other non-limiting examples of the interactions between the healthcare professional 100 and the updated medical record content item 114C' include zoom in, zoom out, click and expand, and return to the user menu 120.

Patient Timeline

In some embodiments, the holographic eyewear 106 can display a timeline of a patient to the healthcare professional 100. The timeline can display time points at which medical records are available for the patient. The healthcare professional 100 can scroll through the timeline to review the patient's medical records at different times. As the healthcare professional 100 scrolls through the timeline, the display of the medical records can change based on the conditions of the patient and the availability of the patient's medical records at different time points. The timeline allows the healthcare professional 100 to monitor the patient's health and disease progression over time.

The healthcare professional 100 can scroll through the timeline, as a graphical input, by "touching" a graphical indicium of the timeline with one of his fingers and "move" the finger to the right, for example, corresponding to moving from a first time point to a later second time point. Image sensors on the eyewear 106 can monitor and capture that movement to determine that the healthcare professional 100 wishes to scroll from the first time point to the second time point. Once the holographic eyewear 106 determines that such a "touch" and "movement" have occurred, the holographic eyewear 106 can display updated medical record content items on the 3D avatar 106. For example, at the first time point, the patient may have liver cancer, and the holographic eyewear 106 can display the medical records relating to the liver cancer as a medical record content item appearing spatially near the 3D avatar's liver. The liver cancer may have metastasized to the patient's lung and brain at the second time point. When the healthcare professional 100 scroll to the second time point, the holographic eyewear 106 can display the medical records relating to the metastasis as two medical record content items appearing spatially near positions of the 3D avatar corresponding to the lung and brain.

Record Creation

Figure 4:
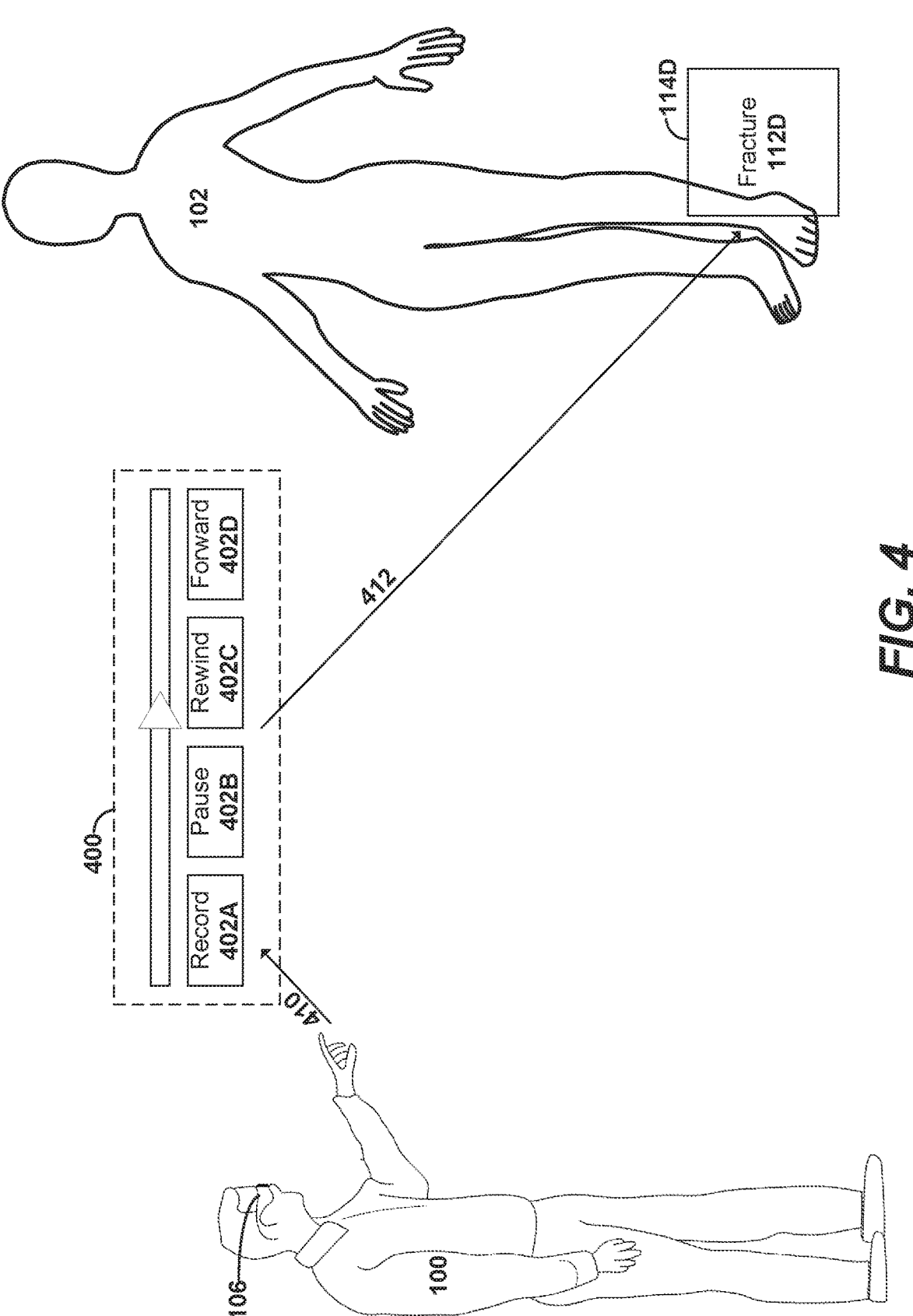
FIG. 4 is a schematic illustration showing the creation of a new medical record and the pinning of a new medical record on the 3D avatar by a healthcare professional.

FIG. 4 is a schematic illustration showing the creation of a new medical record and pinning of the new medical record on a 3D avatar by a healthcare professional 100. During a doctor visit or a hospital visit, the patient may inform the healthcare professional 100 that he is suffering from a new disease or symptom, for example a fracture of the left ankle 112D. To create a new medical record of the fracture of the left ankle 112D, the healthcare professional 100 can "touch" a displayed graphical representation of a submenu content item for creating a new "audio" record. In some embodiments, as the healthcare professional 100 captures and records the new medical record, the holographic eyewear 106 can display a timeline, for example the timeline 302 illustrated in FIG. 3, to the healthcare professional 100.

When the holographic eyewear 106 determines that the healthcare professional 100 has "touched" the displayed graphical representation of the submenu content item for recording a new audio medical record, the holographic eyewear 106 can update the display to show a recording menu content item 400 for recording the new audio medical record. The graphical representation of the recording menu content item 400 can include one or more submenu content items 402A-D. Non-limiting examples of the one or more new submenu content items include a submenu content item 402A for recording the new audio medical record, a submenu content item 402B for pausing the recording of the new audio medical record, a submenu content item 402C for rewinding while recording the new audio medical record, and a submenu content item 402D for fast forwarding while recording the new audio medical record.

Once the holographic eyewear 106 displays the recording menu content item 400 to a healthcare professional 100, he can interact with it by "touching" a displayed graphical representation of the submenu content item 402A for recording the new audio medical record. In one example, the eyewear 106 includes one or more sensors that detect the positions of the healthcare professional's fingers to determine that the content item has been "touched." The holographic eyewear 106 can include one or more microphones for recording the new audio medical record. Once the new audio medical record is created, the healthcare professional 100 can pin 412 the new audio medical record to a pinning location on the left ankle of the 3D avatar 102. The new audio medical record can be displayed as a medical record content item 114D at the pinning location on the fracture of the left ankle 112D. The holographic eyewear 106 can request the healthcare professional 100 to confirm pinning 410 of the new medical record content item 114D to the left ankle of the 3D avatar 102. In some embodiments, the holographic eyewear 106 can determine the pinning location of the new audio medical record, for example, the left ankle of the 3D avatar 102 without the healthcare professional 100 having to pin the medical record at the pinning location. In some embodiments, the holographic eyewear 106 can request the healthcare professional 100 to confirm the pinning location of the new medical record content item 114D that it determines. During subsequent interactions between the healthcare professional 110 and the holographic eyewear 106, it can display the medical record content item 114D to the healthcare professional 110 and other healthcare professionals, at the pinning location.

Holographic Eyewear

FIG. 5 is a block diagram depicting an illustrative operating environment of a holographic eyewear 106, the 3D avatar medical information system 104, and the electronic medical record system 110. While many configurations are possible for the holographic eyewear 106, some embodiments of the holographic eyewear 106 are illustrated in FIG. 5. As illustrated, the holographic eyewear 106 can include a processor 506A that is in electrical communication with a memory 508A, a storage 510A, and a communication interface 512A. The memory 508A stores instructions to configure the processor 506A to perform the functions of or processes implemented by the holographic eyewear 106 when the holographic eyewear 106 is powered on. When the holographic eyewear 106 is powered off, the storage 510A stores the instructions for configuring the processor 506A to perform the functions of the holographic eyewear 106. The communication interface 512A facilitates the communications between the holographic eyewear 106 and other devices connected to the network 108, for example the 3D avatar medical information system 104.

The holographic eyewear 106 can include one or more sensors such as a motion sensor 514A, an orientation sensor 514B, an image sensor 514C, a microphone 514C, and a location sensor 514D in electrical communication with the processor 506A. These sensors may be configured to detect the healthcare professional's movements and the sounds he makes, for example his voice commands to the holographic eyewear 106. These sensors can detect the movements of people and objects in his surrounding, including those that the healthcare professional 100 sees through the lenses of the holographic eyewear 106.

The holographic eyewear 106 can include a healthcare professional identifier 524A and an avatar displayer 526. The healthcare professional identifier 524A is configured to determine the identity of the wearer of the holographic eyewear 106 based on image authentication and biometric authentication with data captured by the one or more sensors 514A-E of the holographic eyewear 106. The avatar displayer 526 is configured to display the 3D avatar 102 to the healthcare professional 100.

The holographic eyewear 106 can include a record retriever 528A, a content item displayer 530, a record creator 532A, a record updater 534A, and a record pinner 536A. The record retriever 528A is configured to retrieve medical records from the electronic medical record system 110. The content item displayer 530 is configured to display medical records to the healthcare professional 100 as content items and timelines. The record creator 532A is configured to create medical records for storage in the electronic medical record system 110. The record updater 534A is configured to update medical records stored in the electronic medical record system 110. The record pinner 536A is configured to allow healthcare professionals to pin medical records to locations on the 3D avatar 102 for display as medical record content items.

The holographic eyewear 106 can include one or more of a patient identifier 538, an instrument identifier 539, a command determiner 540, a 3D avatar medical information system communicator 542A, and a task workflow module 544A. The patient identifier 538 is configured to determine the identity of the patient the healthcare professional sees through the lenses of the holographic eyewear 106 using, for example computer vision algorithms. The instrument identifier 539 is configured to determine the identity of the instrument the healthcare professional sees through the lenses of the holographic eyewear 106. The command determiner 540 is configured to determine the commands given by the healthcare professional 100 to the holographic eyewear 106 based on the one or more sensors. The 3D avatar medical information system communicator 542A and the communication interface 512A are configured to facilitate the communication between the holographic eyewear 106 and the 3D avatar medical information system 104. The task workflow module 544A is configured to inform the healthcare professional 100 of the procedures he should follow under various circumstances.

3D Avatar Medical Information System

While many configurations are possible for the 3D avatar medical information system 104, some embodiments of the 3D avatar medical information system 104 are illustrated in FIG. 5. As illustrated, the 3D avatar medical information system 104 can include a processor 506B that is in electrical communication with a memory 508B, a storage 510B, and a communication interface 512B. The functions of processor 506B, the memory 508B, and the storage 510B are similar to the functions of processor 506A, the memory 508A, and the storage 510A. The communication interface 512B facilitates the communications between the 3D avatar medical information system 104 and other devices connected to the network 108, for example the holographic eyewear 106 and the electronic medical record system 110.

The 3D avatar medical information system 104 can include a healthcare professional identifier 524B configured to determine the identity of the wearer of the holographic eyewear 106. The holographic eyewear 106 can include one or more of a record retriever 528B, a record creator 532B, a record updater 534B, and a record pinner 536B. The record retriever 528B is configured to retrieve medical records 111 stored in the electronic medical record system 110. The record creator 532B is configured to create new medical records for storage in the electronic medical record system 110. The record pinner 536B is configured to store the pinning locations and the associations between the pinning locations and the medical records 111.

The 3D avatar medical information system 104 can include one or more of a task workflow module 544B, an eyewear communicator 550, and an electronic medical record system (EMRS) communicator 552. The task workflow module 544B is configured to determine the appropriate instructions the healthcare professional 100 should follow under various circumstances. The eyewear communicator 550 and the communication interface 512B are configured to facilitate the communication between the 3D avatar medical information system 104 and the holographic eyewear 106. The electronic medical record system communicator 552 and the communication interface 512B are configured to facilitate the communication between the 3D avatar medical information system 104 and the electronic medical record system 110.

Electronic Medical Record System

While many configurations are possible for the electronic medical record system 110, some embodiments of the electronic medical record system 110 are illustrated in FIG. 5. As illustrated, the electronic medical record system 110 can include a processor 506C that is in electrical communication with a memory 508C, a storage 510C, and a communication interface 512C. The functions of processor 506C, the memory 508C, and the storage 510C are similar to the functions of processor 506A, the memory 508A, and the storage 510A. The storage 510C can also store patient medical records. The communication interface 512C facilitates the communications between the electronic medical record system 110 and other devices connected to the network 108, for example the 3D avatar medical information system 104.

The holographic eyewear 106 can include one or more of a record retriever 528C, a record creator 532C, and record updater 534C, and the 3D avatar medical information system communicator 542C. The record retriever 528C is configured to retrieve medical records stored in the storage 510C of the electronic medical record system 110. The record creator 532C is configured to create medical records for storage in the storage 510C of the electronic medical record system 110. The record updater 534C is configured to update medical records stored in the storage 510C. The 3D avatar medical information system communicator 542C and the communication interface 512C are configured to facilitate the communication between the electronic medical record system 110 and the 3D avatar medical information system 104.

In some embodiments, the 3D avatar medical information system 104 can perform some of the functions of or processes implemented by the holographic eyewear 106. In some embodiments, the holographic eyewear 106 can perform some of the functions of or processes implemented by the 3D avatar medical information system 104. In some embodiments, the 3D avatar medical information system 104 can perform some of the functions of or processes implemented by the electronic medical record system 110. In some embodiments, the electronic medical record system 110 can perform some of the functions of or processes implemented by the 3D avatar medical information system 104.

In some embodiments according to the present disclosure, the processor 506A-506C can be configured to store or transmit data to one or more of the memory 508A-508C and the storage 510A-510C respectively. The memory 508A-508C may be utilized by the processor 506A-506C respectively to store data dynamically created during operation of the holographic eyewear 106, the 3D avatar medical information system 104, and the electronic medical record system 110 respectively. The memory 508A-508C may also store dynamic run time data, such as stack or heap data utilized by programs executing on the processor 506A-506C respectively. The storage 510A-510C may be utilized to store data generated by the holographic eyewear 106, the 3D avatar medical information system 104, and the electronic medical record system 110 respectively. For example, commands by the healthcare professional 100 can be stored in the storage 510A-510B. In some embodiments, sensor data from the one or more sensors can be stored in one or more of the memory 508A-508B and the storage 510A-510B.

In some embodiments according to the present disclosure, the memory 508-508C may be considered a computer readable media and stores one or more programs of the holographic eyewear 106, the 3D avatar medical information system 104, and the electronic medical record system 110 respectively. The one or more programs store data values defining instructions for processor 506A-506C. These instructions configure the processor 506A-506C to perform functions of the holographic eyewear 106, the 3D avatar medical information system 104, and electronic medical record system 110 respectively. For example, in some aspects, the memory 508A-508C may be configured to store instructions that cause processor 506A-506C respectively to perform various functions, for example retrieving the medical records 111 requested by the holographic eyewear 106.

The 3D avatar medical information system 104 and the holographic eyewear 106 can communicate with each other through the network 108 using the communication interface 512A-512B respectively. The 3D avatar medical information system 104 and the electronic medical record system 110 can communicate with each other through the network 108 using the communication interface 512B-512C respectively. The communication interface 512A-512C can be connected to the network 108 by wired or wireless communications, cellular communication, Bluetooth®, local area network (LAN), wide local area network (WLAN), radio frequency (RF), infrared (IR), or any other communication method or system known in the art. In some embodiments, the communication interface 512A-512C communicates with one another using cloud connectivity. The 3D avatar medical information system 104 can send data to and receive data from the holographic eyewear 106 using the communication interface 512A-512B, 3D avatar medical information system communicator 542A and the eyewear communicator 550. The 3D avatar medical information system 104 can send data to and receive data from the electronic medical record system 110 using the communication interface 512B-512C and the electronic medical record system communicator 552 and the 3D avatar medical information system 544C.

Sensors

The holographic eyewear can include one or more of the motion sensor 514A, the orientation sensor 514B, the image sensor 514C, the microphone 514D, and the location sensor 514E. The motion sensor 514A can be configured to sense, detect, and determine the movements of the healthcare professional 100 wearing and operating the holographic eyewear 106, for example the healthcare professional's head nod. As illustrated with reference to FIG. 4, when the holographic eyewear 106 requests the healthcare professional 100 confirm the pinning 412 of the new medical record content item 114D to the left ankle of the 3D avatar 102, the healthcare professional 100 can nod his head to indicate his confirmation of the pinning 412 location. In some embodiments, the motion sensor 514A can convert the healthcare professional's motions into electrical signals for processing by the command determiner 540.

Referring to FIG. 5, in some embodiments, the motion sensor 514A can comprise a single axis accelerometer configured such that the accelerometer can sense, detect, and determine the movements imparted on the holographic eyewear 106 by the healthcare professional 100. In some embodiments, the motion sensor 514A can comprise multiple accelerometers, for example single axis accelerometers and 3D accelerometers, to enable detection of direction movement and vibrations in a multiplicity of directions and to increase detection sensitivity.

The orientation sensor 514B can be configured to determine the orientation of the healthcare professional's head relative to a fixed plane, for example the floor of an examination room in a hospital where the healthcare professional 100 is performing an examination. For example, the holographic eyewear 106 can be configured to display the 3D avatar 102 at a fixed orientation relative to the fixed plane. When the healthcare professional 100 tilts his head a certain extent, for example 10°, in one direction, the holographic eyewear 106 can detect such a tilt using the orientation sensor 514B. In response to detecting such a tilt, the holographic eyewear 106 can tilt the display of the 3D avatar 102 to the healthcare professional 100 the same extent, for example 10°, in the opposite direction. Consequently, the healthcare professional 100 sees that the 3D avatar 102 has a fixed orientation relative to the fixed plane. The orientation of the 3D avatar 102 relative to the fixed plane does not change when the orientation of the holographic eyewear 106 changes. In some embodiments, the orientation sensor 514B can convert orientation information into electrical signals for processing by the command determiner 540.

The holographic eyewear 106 can include, for example, two image sensors 514C. The two image sensors 514C enable the holographic eyewear 106 to capture and reconstruct what the healthcare professional 100 sees. One of the two image sensors 514C can be located spatially near the left eye of the healthcare professional 100 and be oriented such that it captures some or all of what the healthcare professional's left eye sees. The other of the two image sensors 514C can be located spatially near the right eye of the healthcare professional 100 and be oriented such that it detects some or all of what the healthcare professional's right eye sees. In some embodiments, the two image sensors 514C convert photons into electrical signals and images for processing by the command determiner 540. In some embodiments, the holographic eyewear 106 can combine, using the processor 506A and the memory 508A, the images from the two image sensors 514C to create stereoscopic images of what the healthcare professional 100 sees with his two eyes. In some embodiments, the holographic eyewear 106 can include one image sensor 514C. The image sensor 514C can be located between the two eyes and be oriented such that it detects and approximates what the healthcare professional 100 sees with his two eyes. In some embodiments, the image sensor 514C can be located at other locations on the holographic eyewear 106.

The holographic eyewear 106 can capture what the healthcare professional 100 sees in his field of view using one or more image sensors 514C. In some embodiments, the holographic eyewear 106 can capture more or less than what the healthcare professional 100 sees in his field of view using the image sensors 514C. As illustrated with reference to FIG. 1, when the healthcare professional 100 sees, through the holographic eyewear 106, that one or more of his fingers, hands, arms, legs, or one or more objects he is connected with, come into contact with a content item, the holographic eyewear 106 can determine that such a contact has occurred. The holographic eyewear 106, using the image sensors 514C, can determine that such a contact has occurred. Consequently, the holographic eyewear 106 can capture and "see" the visual commands that the healthcare professional 100 gives to the holographic eyewear 106. In some embodiments, the holographic eyewear 106 can create a new video medical record or a new image medical record using the image sensors 514C.

The microphone 514C can be configured to detect sound from the environment surrounding the holographic eyewear 106 and from the healthcare professional 100. The holographic eyewear 106 detects and "hears" what the healthcare professional 100 hears and says. As illustrated with reference to FIG. 4, when the holographic eyewear 106 requests the healthcare professional 100 confirm the pinning 412 of the new medical record content item 114D to the left ankle of the 3D avatar 102, the healthcare professional 100 can say "yes" to indicate his confirmation of the pinning 412 location. In some embodiments, the microphone 514C can convert acoustic waves into electrical signals for processing by the command determiner 540.

Referring to FIG. 5, the location sensor 514D can be configured to determine the location of the healthcare professional 100 based on the location of the holographic eyewear 106. Non-limiting examples of the location sensor 514D includes global positioning system (GPS) and assisted GPS (aGPS) transceivers. The holographic eyewear's responses to the healthcare professional's commands can be based on the location of the healthcare professional 100. The holographic eyewear 106 can allow or deny the healthcare professional's commands based on the location of the healthcare professional 100. For example, if the holographic eyewear 106 determines that the healthcare professional 100 is outside a hospital, he may be prohibited from accessing any confidential patient information. In some embodiments, the holographic eyewear 106 can adjust, rearrange, or reorganize the user menu 120, the various content items, and the 3D avatar 102 based on the location of the healthcare professional 100. For example, if the healthcare professional 100 is at a hospital cafeteria, the healthcare professional 100 may not be authorized to order tests for patients. Thus, user menu 120 may not display the "order tests" main menu content item 122B and the submenu content items 140 such as order "MRI" 140A, "X-ray" 140B, "blood test" 140C, and "more" tests 140D.

Healthcare Professional Identifier

Privacy is important for healthcare professionals to successfully manage patient healthcare. To maintain patient privacy, the holographic eyewear 106 can include a healthcare professional identifier 524A in communication with the processor 506. The healthcare professional identifier 524A determines the identity of a wearer of the holographic eyewear 106. Methods for determining the identity of a wearer of the holographic eyewear 106 include image authentication and biometric authentication. For example, the wearer of the holographic eyewear 106 can look into a mirror, and the image sensor 514C can take a picture of the wearer. Based on the picture of the wearer, the healthcare professional identifier 524A can determine the wearer's identity. In some embodiments, the healthcare professional identifier 524A can send the identity of the wearer to the healthcare professional identifier 524B of the 3D avatar medical information system 104. In some embodiments, the healthcare professional identifier 524A can send the image of the wearer to the healthcare professional identifier 524B for determination of the wearer's identity.

Based on the wearer's identity, the holographic eyewear 106 can determine whether the wearer is an authorized healthcare professional and whether an authorized healthcare professional is authorized to carry out certain interactions with the holographic eyewear 106. For example, if an authorized healthcare professional is a medical doctor, he can be authorized to order tests for his patients and not other patients. If an authorized healthcare professional is a hospital administrative staff, he may be not authorized to order tests for patients. The hospital administrative staff may be authorized to review a patient's payment history.

Avatar Display

The holographic eyewear 106 can include an avatar displayer 526 in communication with the processor 506A.

The avatar displayer 526 determines the characteristics of the 3D avatar 102 shown to the healthcare professional 100 on the lenses of the holographic eyewear 106. Non-limiting examples of the characteristics of the 3D avatar 102 include color, opacity, size, orientation, and location. In some embodiments, the avatar displayer 526 can determine the size of the 3D avatar 102 based on the weight and height of the patient. The avatar displayer 526 can determine the size of the 3D avatar 102 based on, for example, the number and the sizes of the various content items the lenses of the holographic eyewear 106 shows to the healthcare professional 100. The avatar displayer 526 can determine the location of the 3D avatar 102 based on, for example, the colors, opacities, sizes, orientations, and locations of other objects in the holographic eyewear's field of view. Non-limiting examples of other objects include patients, doctor office furniture, and medical instruments. For example, the avatar displayer 526 can display the 3D avatar 102 on the lenses of the holographic eyewear 106 such that the 3D avatar 102 coincide with or overlap the patient. As another example, the avatar displayer 526 can display the 3D avatar 102 on the lenses of the holographic eyewear 106 such that the 3D avatar 102 is adjacent to the patient. The avatar displayer 526 can determine the color of the 3D avatar 102 based on, for example, the colors of other objects in the holographic eyewear's field of view.

Record Retrieval, Display, Creation, and Pinning

The holographic eyewear 106 can include one or more of the record retriever 528A, the content item displayer 530, the record creator 532A, the record updater 534A, and the record pinner 536A in communication with the processor 506A. The record retriever 528A (in conjunction with the record retriever 528B of the 3D avatar medical information system 104 and the record retriever 528C of the electronic medical record system 110) can retrieve medical records 111 stored in the electronic medical record system 110. To retrieve medical records 111 stored in the electronic medical record system 110, the record retriever 528A can send one or more requests for medical records 111 to the record retriever 528B of the 3D avatar medical information system 104. Based on the identity of the healthcare professional 100 determined by, for example, the healthcare professional identifier 524A, the record retriever 528B can retrieve the requested medical records 111 from the record retriever 528C of the electronic medical record system 110. The record retriever 528B then can send the requested medical records 111 retrieved from the electronic medical record system 110 to the holographic eyewear 106. The record retriever 528C can grant or deny access to the requested medical records 111 based on the identity of the healthcare professional 100 and the authorization of the 3D avatar medical information system 104.

The content item displayer 530 can display the various content items at various locations on the lenses of the holographic eyewear 106. The content item displayer 530 can determine the locations of the various content items on the lenses of the holographic eyewear 106. In some embodiments, the content item displayer 530 can display some or all of the medical records 111 retrieved from the electronic medical record system 110 to the healthcare professional 100. The content item displayer 530 can display the retrieved medical records 111 as medical record content items, for example medical record content item 114A-D, at particular locations on the lenses of the holographic eyewear 106. In some embodiments, the locations of the medical record content items 114 are the pinning locations decided by the healthcare professional 100 when creating the medical record content item 114A-D. As illustrated with reference to FIG. 4, the pinning location of the medical record content item 114D can be the left ankle of the 3D avatar 102, determined by the healthcare professional 100 when creating the medical record content item 114. In some embodiments, the particular locations may be relative to the location of the 3D avatar 102 on the lenses of the holographic eyewear 106.

As illustrated with reference to FIG. 1, the content items 114 can include the medical records 111. For the content item displayer 530 to display the content items of the "headache" category 112A, the record retriever 528A may retrieve some or all of the patient's medical records 111 of the "headache" category 112A. When the healthcare professional 100 "touches" 170 the medical record content item 114B of the "rash" category 112B, the record retriever 528A can retrieve some or all of the patient's medical records 111 of the "rash" category for display by the content item displayer 530. The content item display 530 can display the patient's medical records 111 as the updated medical record content item 114B' as illustrated with reference to FIG. 2. For the content item displayer 530 to display the medical record content items 312A-312C as a timeline, the record retriever 528A can retrieve some or all of the patient's medical records 111 of the "burn" category 112C as illustrated with reference to FIG. 3. To display the video medical record of the medical record content item 312C, the record retriever 528A can retrieve some or all of the video medical record for display by the content item displayer 530.

Referring to FIG. 5, the record creator 532A (in conjunction with the record creator 532B of the 3D avatar medical information system 104 and the record creator 532C of the electronic medical record system 104) enables the healthcare professional 100 to create and store new medical records. The electronic medical record system 110 can store new medical records in the storage 510C. As illustrated with reference to FIGS. 1 and 4, to create a new medical record, the healthcare professional 100 can "touch" 174, for example, the submenu content item 160B for creating a new "audio" record. When the holographic eyewear 106 determines that the healthcare professional 100 has "touched" 174 the displayed graphical representation of the submenu content item 160B for recording a new audio medical record, the content item displayer 530 can update the display shown to the healthcare professional 100. The content item displayer 530 can display the new menu content item 400 for recording the new audio medical record. Once the healthcare professional 100 confirms the creation of the new audio medical record is complete, the record creator 532A sends the new audio medical record to the record creator 532B for storage in the storage 510C by the record creator 532C of the electronic medical record system 110.

Referring to FIG. 5, the record updater 534A enables the healthcare professional 100 to update the medical records 111 stored in the storage 510C of the electronic medical record system 110. In some embodiments, the record updater 534A can update the contents of existing medical records 111. The record updater 534A (in conjunction with the record updater 534B of the 3D avatar medical information system 104 and the record updater 534C of the electronic medical record system 110) can update the medical records 111 stored in the storage 510C. In some embodiments, the record updater 534A (in conjunction with the record creator 532A) can store the updated medical records as new medical records in the storage 510C.

The record pinner 536A allows healthcare professionals to pin medical records to locations on the 3D avatar 102 for display as medical record content items. The record pinner 536A (in conjunction with the command determiner 540) can determine the pinning locations. As illustrated with reference to FIG. 4, once a new audio medical record is generated, the healthcare professional 100 can pin 412 the new audio medical record to a pinning location. For example, the pinning location can be the left ankle of the 3D avatar 102. The new audio medical record can be displayed as a medical record content item 114D at the pinning location on the left ankle 112D of the 3D avatar 102. In some embodiments, the record pinner 536A can determine the pinning location of the new audio medical record, for example, the left ankle of the 3D avatar 102 without the healthcare professional 100 having to pin the medical record at the pinning location. In some embodiments, the record pinner 536A can request the healthcare professional 100 to confirm the pinning location of the new medical record content item 114D. During subsequent interactions between the healthcare professional 110 and the holographic eyewear 106, the content item displayer 530 can display the medical record content item 114D at the pinning location provided by the record pinner 536A.

In some embodiments, the record pinner 536A allows the healthcare professional 110 to update the pinning locations of medical records with existing pinning locations. For example, the content item displayer 530 can display the new audio medical record as the medical record content item 114D at the pinning location on the left ankle 112D of the 3D avatar 102. The healthcare professional 110 can move the pinning location, for example, from the left ankle to the right ankle of the 3D avatar 102. In some embodiments, the record pinner 536A allows the healthcare professional 110 to create pinning locations for existing medical records 111 stored in the storage 510C without existing pinning locations.

Once the pinning locations are determined, the record pinner 536A can send the pinning locations to the record pinner 536B of the 3D avatar medical information system 104. The record pinner 536B can store the pinning locations and the associations between the pinning locations and the medical records 111 in the storage 510B. The record pinner 536B can provide the record pinner 536A with the pinning locations of the medical records 111, based on the pinning locations and the associations between the medical records 111 in the storage 510B. The content item displayer 530 can display the medical records 111 at appropriate locations in the healthcare professional's field of view as the medical record content items 114 based on the pinning locations of the medical records 111 provided by the record pinner 536B to the record pinner 536A.

Patient Identification

The holographic eyewear 106 can include a patient identifier 538 in communication with the processor 506A. The patient identifier 538 can determine the identities of patients. For example, the patient identifier 538 can determine the identity of the patient the healthcare professional 100 sees through the holographic eyewear's one or more lenses, based on the images of the patient captured by the image sensors 514C. In some embodiments, the patient identifier 538 can determine the identity of the patient the healthcare professional 100 sees based on the patient's voice captured by the microphone 514C. Based on the identity of the patient determined by the patient identifier 538, the holographic eyewear 106 can display the appropriate user menu 120, the appropriate content items, and the appropriate 3D avatar 102 to the healthcare professional 100.

Instrument Identification

In some embodiments, the holographic eyewear 106 can include an instrument identifier 539 in communication with the processor 506A. The instrument identifier 539 can determine the identities of instruments. The identity of an instrument can include, for example, the instrument's make, model, year of manufacture, usage history, and service history. For example, the instrument identifier 539 can determine the identity of the instrument the healthcare professional 100 sees through the holographic eyewear's lenses, based on the images of the instrument captured by the image sensors 514C. In some embodiments, the instrument identifier 539 can determine the identity of the instrument the healthcare professional 100 based on the sound wave emitted by the instrument captured by the microphone 514C. Based on the identity of the instrument determined by the instrument identifier 539, the holographic eyewear 106 can display, for example, an instruction menu of the instrument for the healthcare professional 100 to review.

Command Determination

The holographic eyewear 106 can include a command determiner 540 in communication with the processor 506A. The command determiner 540 (in conjunction with the one or more sensors of the holographic eyewear 106) can determine the commands the healthcare professional 100 gives to the holographic eyewear 106. Thus, the healthcare professional 100 can interact with the holographic eyewear 106 and the 3D avatar medical information system 104 through the command determiner 540 and the one or more sensors 514.

In some embodiments, the one or more image sensors 514C are located and oriented on the holographic eyewear 106 such that they can capture what the healthcare professional 100 sees. The holographic eyewear 106, using the image sensors 514C, can capture and "see" the movements of the healthcare professional's fingers, hands, arms, legs, and one or more objects he is connected with. The command determiner 540, based on the images captured by the image sensors 514C, can determine that these movements are visual commands given by the healthcare professional 100. Based on the visual commands, the holographic eyewear 106 can update the display shown to the healthcare professional 100 on its lenses. As illustrated with reference to FIG. 1, the command determiner 540 (in conjunction with the image sensors 514C) can determine that healthcare professional 100 has "touched" the graphical representation of a content item. Based on the identity of the content item, the command determiner 540 can determine the specific command given by the healthcare professional 100, for example to see a disease timeline. As illustrated with reference to FIG. 2, the command determiner 540 can determine that the healthcare professional 100 has moved two of his fingers away from each other 204. Based on the specific movement, the command determiner 540 can determine the specific command given by the healthcare professional 100, for example, to zoom in on the updated medical record content item 114B'.

Referring to FIG. 5, in some embodiments, the holographic eyewear 106, using the one or more motion sensors 514A, can detect the healthcare professional's head nods. The command determiner 540, based on the electrical signals produced by the motion sensor 514A, can determine that these movements are motion commands given by the healthcare professional 100. Based on the motion commands, the holographic eyewear 106 can update the display shown to the healthcare professional 100.

In some embodiments, the holographic eyewear 106, using the one or more microphones 514C, can determine the words that the healthcare professional 100 has said. The command determiner 540, based on the signals produced by the one or more microphones 514C and one or more speech recognition methods, can determine that the words are verbal commands given by the healthcare professional 100. Based on the verbal commands, the holographic eyewear 106 can update the display shown to the healthcare professional 100.

Instructions in the command determiner 540 can configure the processor 506A to determine the commands given by the healthcare professional 100. In some embodiments, the command determiner 540 can include instructions that configure the processor 506A to interpret and apply one or more filters to the data received from the one or more sensors. For example, the command determiner 540 can include instructions that configure the processor 506A to apply one or more filters to interpret the acoustic waveforms captured by the microphone 514C, for example, to remove noise from the healthcare professional's environment captured by the microphone 514C.

Instructions in the command determiner 540 can also configure the processor 506A to extract command parameters from the data received by the one or more sensors. Non-limiting examples of command parameters include the types of commands and the numeric values of the commands. As illustrated with reference to FIG. 2, the command determiner 540 can determine that the healthcare professional 100 has moved two of his fingers away from each other 204. The command type for such movement can be, for example, zoom in or zoom out. The command parameter can be, for example, the extent of zoom in based on the magnitude of the two fingers moving away from each other. Therefore, instructions in the command determiner 540 may configure the processor 505A for interpreting, filtering, and analyzing the signals, whether raw or processed, from sensors.

Task Workflow Displayer

The holographic eyewear 106 can include a task workflow displayer 544A in communication with the processor 506A. The 3D avatar medical information system 104 can include the task workflow displayer 544B in communication with the processor 506B. The task workflow displayer 544A, with the task workflow displayer 544B, can determine the appropriate instructions the healthcare professional 100 should follow for a given task. The task workflow displayer 544A can store instructions the healthcare professional 100 should follow for various tasks in the storage 510A. In some embodiments, the task workflow displayer 544B can store instructions the healthcare professional 100 should follow for various tasks in the storage 510B. The task workflow displayer 544B can provide the task workflow displayer 544A with instructions stored for various tasks stored in the storage 510B that the healthcare professional 100 should follow.

For example, to locate veins in a patient's arm for blood draw, the task workflow displayer 544A can display instructions, on the holographic eyewear's lenses, to the healthcare professional 100 that he should follow in order to successfully locate veins in the patient's arm for blood draw. For example, to insert a catheter into a patient, the task workflow displayer 544A can display instructions, on the holographic eyewear's lenses, to the healthcare professional 100 that he should follow in order to successfully insert a catheter into the patient. In some embodiments, the task workflow displayer 544A can display instructions to the healthcare professional 100 to facilitate his compliance with procedures mandated by the hospital, the city, the state, or the federal government.

Communication between the Eyewear, the 3D Avatar Medical Information System, and the Electronic Medical Record System The holographic eyewear 106 can include a 3D avatar medical information communicator 542A in communication with the processor 506A and the communication interface 512A. The 3D avatar medical information system 104 can include the eyewear communicator 550 in communication with the processor 506B and the communication interface 512B. The 3D avatar medical information communicator 542A and the eyewear communicator 550, together with the communication interface 512A-512B, facilitate the communication between the holographic eyewear 106 and the 3D avatar medical information system 104. In some embodiments, the 3D avatar medical information communicator 542A and the eyewear communicator 550, together with the communication interface 512A-512B, facilitate the communication between the healthcare professional identifier 524A-524B, the record retriever 528A-528B, the record creator 532A-532B, the record updater 534A-534B, the record pinner 536A-536B, and the task workflow displayer 544A-544B.

The 3D avatar medical information system 104 can include the electronic medical record system communicator 552 in communication with the processor 506B and the communication interface 512B. The electronic medical record system 110 can include the 3D avatar medical information communicator 542C in communication with the processor 506C and the communication interface 512C. The electronic medical record system communicator 550 and the 3D avatar medical information communicator 542A, together with the communication interface 512B-512C, facilitate the communication between the 3D avatar medical information system 104 and the electronic medical record system 110. In some embodiments, the electronic medical record system communicator 550 and the 3D avatar medical information communicator 542A, together with the communication interface 512B-512C, can facilitate the communication between the record retriever 528B-528C, the record creator 532B-532C, and the record updater 534B-534C.

As will be appreciated by one skilled in the art, there are numerous ways of carrying out the examples, improvements, and arrangements of a 3D avatar medical information system and a holographic eyewear in accordance with embodiments of the present invention. Although references have been made to the illustrative embodiments depicted in the drawings and the above description, the embodiments disclosed herein are not meant to be exhaustive of the various alternative designs and embodiments that are disclosed. Those skilled in the art will readily appreciate that various modifications may be made, and various combinations can be made, without departing from the invention.

In the above description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, or a subprogram, etc. When a process corresponds to a software function, its termination corresponds to a return of the function to the calling function or the main function.

Those of skill in the art will understand that information and signals may be represented using any of a variety of different technologies and techniques. For example, data, instructions, commands, information, signals, bits, symbols, and chips that may be referenced throughout the present disclosure may be represented by voltages, currents, electromagnetic waves, magnetic fields or particles, optical fields or particles, or any combination thereof.

The above detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways, without materially departing from the novel teachings and advantages of this invention. Accordingly, all such modifications are intended to be included within the scope of the invention. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

Furthermore, the system and methods described herein may be implemented by a 3D avatar medical information system and a holographic eyewear in communication with a computing device. These include mobile and non-mobile devices, as well as general purpose or special purpose computing system environments or configurations. Examples of computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. Further, the systems and methods may be implemented in mobile devices. Non-limiting examples of mobile devices include phones, smartphones, Personal Digital Assistants (PDAs), Ultra-Mobile Personal Computers (UMPCs), and Mobile Internet Devices (MIDs).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It should be understood that any reference to an element herein using a designation such as "first," "second," and so forth does not generally limit the quantity or order of those elements. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of: A, B, or C" used in the description or the claims means "A or B or C or any combination of these elements."

As used herein, a phrase referring to "at least one of" a list of items refers to any combination of those items, including single members. As an example, "at least one of: a, b, or c" is intended to cover: a, b, c, a-b, a-c, b-c, and a-b-c.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g.,"a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g.,"a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The steps of a method or process described in connection with the implementations disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of non-transitory storage medium known in the art. An exemplary computer-readable storage medium is coupled to the processor such the processor can read information from, and write information to, the computer-readable storage medium. In the alternative, the storage medium may be integral to the processor. The processor and the storage medium may reside in an ASIC. The ASIC may reside in a user terminal, camera, or other device. In the alternative, the processor and the storage medium may reside as discrete components in a user terminal, camera, or other device.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. The word "exemplary" is used exclusively herein to mean "serving as an example, instance, or illustration." Any implementation described herein as "exemplary" is not necessarily to be construed as preferred or advantageous over other implementations. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of the embodiments of the present disclosure as implemented.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Headings are included herein for reference and to aid in locating various sections. These headings are not intended to limit the scope of the concepts described with respect thereto. Such concepts may have applicability throughout the entire specification.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A device for displaying and recording medical information of a patient to a user using a three-dimensional (3D) avatar, comprising:

holographic eyewear configured to be worn by a user and to display a three dimensional avatar of a patient, wherein the holographic eyewear comprises one or more sensors configured to capture input commands based on the position and gestures of the user's fingers; and a processor configured to:

authenticate the user based on data captured by one or more sensors from the holographic eyewear;

determine a patient identifier based on images of the patient captured by the holographic eyewear;

retrieve medical records of the patient based on the patient identifier;

present, on the holographic eyewear, a three-dimensional avatar representing a patient at an apparent position in 3D space overlapping or adjacent to the patient, wherein the size of the avatar relates to the weight and height of the patient, and the three dimensional avatar is rotatable in space so it can be oriented with the position of the patient, and wherein the three dimensional avatar comprises graphical representations for medical information categories relating to disease types retrieved from the medical records of the patient, and displayed spatially near or overlapping associated body parts of the 3D avatar;

in response to the user selecting a graphical representation for a medical information category relating to a disease type, highlight, on the holographic eyewear, a body part of the 3D avatar associated with the selected medical information category relating to the disease type;

determine, by the image sensor, a first touch input gesture command by the user to view medical records associated with the highlighted body part in 3D space;

in response to the first touch gesture input command, display, to the user using the holographic eyewear, a graphical indicium of a first timeline of medical records linked to the highlighted body part of the patient, the graphical indicium of the first timeline comprising a first plurality of time points corresponding to a progression of a disease in the disease type in the patient, wherein the time points on the first timeline comprise graphical indicia of medical records associated with the disease that can be selected by the user;

determine a second touch input command by the user to display a modified timeline of a second plurality of time points from the progression of the disease of the patient when the image sensor captures the user moving an apparent point of contact with the graphical indicium of the first timeline horizontally in 3D space; and in response to the second touch input command, replace the display of the graphical indicium of the first timeline with a modified graphical indicium corresponding to the modified timeline and the second plurality of time points, wherein the modified timeline comprises a second plurality of graphical indicia representing a second plurality of medical records of the patient.

2. The device of claim 1, wherein the second plurality of time points precedes the first plurality of time points, and wherein the second plurality of medical records of the patient corresponds to the medical information of the patient taken in the second plurality of time points.

3. The device of claim 1, wherein the second plurality of time points follows the first plurality of time points, and wherein the second plurality of medical records of the patient corresponds to medical information of the patient recorded during the second plurality of time points.

4. The device of claim 1, wherein the graphical indicium of the first plurality of time points is displayed at the body part as appearing on top of, overlapping, adjacent to, or behind the 3D avatar.

5. The device of claim 1, wherein the first plurality of time points and the second plurality of time points overlap, and wherein the first plurality of medical records of the patient comprises a medical record of the second plurality of medical records of the patient.

6. The device of claim 1, wherein a first plurality of graphical indicia are displayed as appearing horizontally to the user.

7. The device of claim 1, wherein a first graphical indicium of a first plurality of graphical indicia represents a summary of a first medical record of the first plurality of medical records of the patient.

8. The device of claim 1, wherein the processor is further configured to:

determine a third touch input command of the user that indicates a selection of a second graphical indicium by the user; and retrieve a second medical record from an electronic medical record system.

9. The device of claim 8, wherein the processor is further configured to receive updated medical information from the user and update the second medical record to include the updated medical information.

10. The device of claim 9, wherein the updated medical information comprises written medical information of the user, visual medical information of the user, audio medical information of the user, or any combination thereof.

11. The device of claim 1, wherein the processor is further configured to receive updated medical information of the patient from the user and create a new medical record of the patient.

12. The device of claim 1, wherein the holographic eyewear comprises a virtual reality (VR) headset.

13. The device of claim 12, wherein the processor is configured to receive instructions from the user through a gesture interface.

14. The device of claim 12, wherein the processor is configured to detect the first touch input command from the VR headset worn by the user.

15. The device of claim 14, wherein the processor is further configured to display to the user, via the holographic eyewear, whether the first touch input command has occurred.

16. The device of claim 1, wherein the image sensor is configured to detect and provide positional information in three-dimensional space of one or more fingers, hands, arms, or legs of the user.

17. The device of claim 1, wherein authenticating the user based on data captured by one or more sensors from the holographic eyewear comprises taking a picture of the user to determine the user's identity.

* * * * *